United States Patent [19]

Lok

[11] Patent Number: 5,443,947
[45] Date of Patent: Aug. 22, 1995

[54] HEAT STABILIZED SILVER CHLORIDE PHOTOGRAPHIC EMULSIONS CONTAINING THIOSULFONATE/SULFINATE COMPOUNDS

[75] Inventor: Roger Lok, Rochester, N.Y.

[73] Assignee: Eastman Kodak Company, Rochester, N.Y.

[21] Appl. No.: 159,877

[22] Filed: Nov. 30, 1993

[51] Int. Cl.$^6$ .................... G03C 1/34; G03C 1/035
[52] U.S. Cl. .................... 430/569; 430/567; 430/603; 430/611; 430/600
[58] Field of Search ............ 430/603, 611, 567, 569, 430/600

[56] References Cited

U.S. PATENT DOCUMENTS

| | | | |
|---|---|---|---|
| H706 | 11/1989 | Takahashi et al. | 430/551 |
| T866,036 | 9/1969 | Kalenda et al. | 430/611 |
| 2,057,764 | 10/1936 | Brunden | 430/510 |
| 2,385,762 | 9/1945 | Mueller | 430/607 |
| 2,394,198 | 2/1946 | Mueller | 430/607 |
| 2,440,110 | 4/1948 | Mueller | 430/607 |
| 2,440,206 | 4/1948 | Mueller | 430/607 |
| 3,042,521 | 7/1962 | Dersch et al. | 430/508 |
| 3,043,696 | 7/1962 | Herz et al. | 430/603 |
| 3,057,725 | 10/1962 | Herz et al. | 430/611 |
| 3,226,232 | 12/1965 | Dersch et al. | 430/401 |
| 3,301,678 | 1/1967 | Humphlett et al. | 430/352 |
| 3,338,918 | 8/1967 | Geselbracht et al. | 260/314.5 |
| 3,397,986 | 8/1968 | Millikan et al. | 430/603 |
| 3,447,925 | 6/1969 | Dersch et al. | 430/423 |
| 3,466,173 | 9/1969 | Ishikawa et al. | 430/566 |
| 3,615,534 | 10/1971 | Tajima et al. | 430/608 |
| 3,759,901 | 9/1973 | Lincoln et al. | 548/156 |
| 3,761,277 | 9/1973 | Vandenberghe et al. | 430/551 |
| 3,880,864 | 4/1975 | Lincoln et al. | 546/174 |
| 4,058,524 | 11/1977 | Leshin | 544/136 |
| 4,198,240 | 4/1980 | Mikawa | 430/570 |
| 4,245,033 | 1/1981 | Eida et al. | 430/353 |
| 4,276,374 | 6/1981 | Mifune et al. | 430/611 |
| 4,396,707 | 8/1983 | von Konig et al. | 430/446 |
| 4,410,619 | 10/1983 | Kubbota et al. | 430/234 |
| 4,451,557 | 5/1984 | Lok et al. | 430/505 |
| 4,511,644 | 4/1985 | Okamura et al. | 430/219 |
| 4,547,452 | 10/1985 | Toya | 430/216 |
| 4,620,205 | 10/1986 | Iiyama et al. | 346/208 |
| 4,620,941 | 11/1986 | Yoshikawa et al. | 252/408.1 |
| 4,770,987 | 9/1988 | Takahashi et al. | 430/546 |

(List continued on next page.)

FOREIGN PATENT DOCUMENTS

| | | |
|---|---|---|
| 138622 | 4/1985 | European Pat. Off. . |
| 267483 | 5/1988 | European Pat. Off. . |
| 293917 | 12/1988 | European Pat. Off. . |
| 294149 | 12/1988 | European Pat. Off. . |
| 297804 | 1/1989 | European Pat. Off. . |
| 305926 | 3/1989 | European Pat. Off. . |
| 327272 | 8/1989 | European Pat. Off. . |
| 348934 | 1/1990 | European Pat. Off. . |
| 349286 | 1/1990 | European Pat. Off. . |
| 358170 | 3/1990 | European Pat. Off. . |
| 368304 | 5/1990 | European Pat. Off. . |
| 369491 | 5/1990 | European Pat. Off. . |
| 371338 | 6/1990 | European Pat. Off. . |
| 434012 | 6/1990 | European Pat. Off. . |
| 435270 | 7/1991 | European Pat. Off. . |
| 435355 | 7/1991 | European Pat. Off. . |
| 439041 | 7/1991 | European Pat. Off. . |
| 447105 | 9/1991 | European Pat. Off. . |
| 447647 | 9/1991 | European Pat. Off. . |
| 495253 | 7/1992 | European Pat. Off. . |
| 2741261 | 3/1979 | Germany . |
| 3307506 | 9/1984 | Germany . |
| 54-069428 | 6/1979 | Japan . |

(List continued on next page.)

*Primary Examiner*—Charles L. Bowers, Jr.
*Assistant Examiner*—Mark F. Huff
*Attorney, Agent, or Firm*—Peter C. Cody

[57] ABSTRACT

A compound represented by Formula I $$MO_2S-Z-SO_2SM^1 \qquad (I)$$

wherein Z is a non-metallic arylene, alkylene or heterocyclic group, and M and $M^1$ are independently cationic counter ions and the use of said compound in a silver halide photographic element comprising a silver halide emulsion which is greater than 50 mole % silver chloride.

15 Claims, No Drawings

U.S. PATENT DOCUMENTS

| | | | |
|---|---|---|---|
| 4,780,404 | 10/1988 | Sills et al. | 430/572 |
| 4,859,580 | 8/1989 | Aono et al. | 430/617 |
| 4,863,846 | 9/1989 | Tanaka et al. | 430/572 |
| 4,914,015 | 4/1990 | Philip, Jr. et al. | 430/572 |
| 4,939,072 | 7/1990 | Morigaki et al. | 430/372 |
| 4,960,689 | 10/1990 | Nishikawa et al. | 430/603 |
| 4,962,016 | 10/1990 | Chino et al. | 430/603 |
| 5,006,448 | 4/1991 | Szajewski et al. | 430/505 |
| 5,006,665 | 4/1991 | Rody et al. | 549/28 |
| 5,009,992 | 4/1991 | Friedrich et al. | 430/573 |
| 5,043,259 | 8/1991 | Arai | 430/569 |
| 5,070,007 | 12/1991 | Rody et al. | 430/551 |
| 5,070,008 | 12/1991 | Maekawa et al. | 430/567 |
| 5,079,138 | 1/1992 | Takada | 430/567 |
| 5,082,766 | 1/1992 | Nishijima et al. | 430/551 |
| 5,084,376 | 1/1992 | Suda et al. | 430/617 |
| 5,091,294 | 2/1992 | Nishijima et al. | 430/505 |
| 5,110,719 | 5/1992 | Shuto et al. | 430/611 |
| 5,229,263 | 7/1993 | Yoshida et al. | 430/600 |
| 5,356,770 | 10/1994 | Lok et al. | 430/600 |

FOREIGN PATENT DOCUMENTS

| | | |
|---|---|---|
| 55-142331 | 11/1980 | Japan . |
| 55-144236 | 11/1980 | Japan . |
| 61-261737 | 11/1986 | Japan . |
| 62-270949 | 11/1987 | Japan . |
| 62-299963 | 12/1987 | Japan . |
| 63-037348 | 2/1988 | Japan . |
| 63-037349 | 2/1988 | Japan . |
| 63-044650 | 2/1988 | Japan . |
| 1-196034 | 8/1989 | Japan . |
| 1-196050 | 8/1989 | Japan . |
| 2-020857 | 1/1990 | Japan . |
| 2-033141 | 2/1990 | Japan . |
| 2-148031 | 6/1990 | Japan . |
| 2-148033 | 6/1990 | Japan . |
| 2-161423 | 6/1990 | Japan . |
| 2-301744 | 12/1990 | Japan . |
| 3-033842 | 2/1991 | Japan . |
| 3-041438 | 2/1991 | Japan . |
| 3-208041 | 9/1991 | Japan . |
| 4-083241 | 3/1992 | Japan . |
| 4-122923 | 4/1992 | Japan . |
| 4-156448 | 5/1992 | Japan . |
| 4-174426 | 6/1992 | Japan . |
| 609818 | 10/1948 | United Kingdom . |
| 1308938 | 3/1973 | United Kingdom . |
| 92/12462 | 7/1992 | WIPO . |

HEAT STABILIZED SILVER CHLORIDE PHOTOGRAPHIC EMULSIONS CONTAINING THIOSULFONATE/SULFINATE COMPOUNDS

FIELD OF THE INVENTION

This invention relates to the use of addenda in silver halide photographic elements to improve heat stability.

BACKGROUND OF THE INVENTION

Photofinishers that use photosensitive paper to produce color prints desire short processing times in order to increase output. One way of obtaining rapid processing is to accelerate the development time by increasing the chloride content of the emulsions used in the photographic paper. However, as the chloride content of a photographic emulsion is increased, it becomes more difficult to obtain good invariant photosensitivity.

One of the problems with silver chloride emulsions is their severe propensity to storage deterioration. Photographic emulsions that have a high silver chloride content are prone to fog increase due to high temperature and humidity during storage. These changes may vary from layer to layer resulting in color imbalance and a loss of quality of the print material. Attempts have been made to reduce fog formation during storage by addition of inhibitory agents to the silver halide emulsions. For example, U.S. Pat. Nos. T866,036; 2,440,110; 3,043,696; 3,057,725; 3,226,232; 3,397,986; 3,447,925; and 3,761,277 describe the addition of organic disulfides to silver halide emulsions to lessen the tendency towards fog growth.

High chloride content color print paper also has an undesirable sensitivity to temperature changes during exposure. For example, when the temperature upon exposure rises due to heat from the exposing element during printing, the print density changes if the printing conditions are left at the initial set values. This may result in prints varying in density that were exposed at the normal temperature. Very often, an increase in temperature during exposure of the paper may result in a selective increase in speed in one layer, for instance the cyan layer, over another light sensitive layer such as the magenta layer. This results in improper color balance of the color print, and requires the photofinisher to readjust his printing conditions in order to compensate for this density fluctuation. This results in a loss in operating efficiency.

This deficiency in the use of high silver chloride color paper material is recognized in the art. In particular, EP 0 367,227 (1988) discusses reducing heat sensitivity by employing certain spectral sensitizing dyes in combination with mercapto azoles. However, these dye structures have not proved to be entirely satisfactory in terms of minimizing thermal sensitivity while still maintaining optimal sensitization efficiency. EP 0 325,235 describes using iron ion donating compounds in high chloride photographic elements to reduce their change in sensitivity due to exposure at elevated temperature. Despite these attempts to address the thermal problem, no solution has been found which completely eliminates the above concerns.

U.S. Pat. No. 5,043,259 describes using alkyl and aryl disulfinates in the formation of pre-fogged direct positive silver halide emulsions. U.S. Pat. No. 4,939,072 describes using sulfinates as storage stability improving compounds in color photographs. U.S. Pat. 4,770,987 describes using sulfinates as anti-staining agents along with a magenta coupler in silver halide materials. EP 0 463,639, describes using sulfinic acid derivatives as dye stabilizers. U.S. Pat. No. 4,410,619 describes using a sulfinic acid salt to treat a paper base to prevent discoloration of the photographic material. U.S. Pat. No. 3,466,173 describes using aromatic sulfinates as stabilizers in a direct positive photographic material. EP 0 267,483 describes adding sulfinates during the sensitization of silver bromide emulsions. Similarly, GB 1,308,938 describes using sulfinates during processing of a silver halide photographic material to minimize discoloration of the image tone. U.S. Pat. No. 2,057,764 describes sulfinates as having fog reducing properties.

U.S. Pat. No. 5,110,719 describes using the combination of thiosulfonates with sulfinates and nucleating agents in a direct positive internal latent image core/shell chlorobromide emulsion. U.S. Pat. No. 3,615,534 describes using a combination of iodate ions and sulfinates to prevent yellow fog in silver halide materials. WO 92/12,462 describes using thiosulfonates and sulfinates in controlling speed increase on incubation of color photographic materials. JP 3,208,041 describes using the combination of thiosulfonates with sulfinates in the sensitization of chloride emulsions for color paper. U.S. Pat. No. 2,440,206 describes using the combination of sulfinates along with small amounts of polythionic acids to stabilize photographic emulsions against fog growth. U.S. Pat. No. 2,440,110 describes using the combination of sulfinates with aromatic or heterocyclic polysulfides in controlling fog growth. U.S. Pat. No. 2,394,198 describes using sulfinates with thiosulfonates in stabilizing silver halide emulsions. The use of sulfinates has been described as reducing stain in photographic paper when used in combination with sulfonates in U.S. Statutory Invention Registration H706, and in EP 0 305,926.

U.S. Pat. No. 4,960,689 describes using thiosulfonates in the finish in high Cl emulsions. Aromatic dithiosulfonic acids are described in U.S. Pat. No. 5,009,992 as supersensitizers in an IR-sensitive high Cl emulsion. U.S. Pat. No. 5,079,138; U.S. Pat. No. 5,016,614; EP 0 368,304; EP 0 369,491 and EP 0 371,338 describe using dithiosulfonate to control reduction sensitization in tabular emulsions. EP 0 434,012 and EP 0 435,270 describe using dithiosulfonates during grain formation.

It is well known in the chemical literature that thiosulfonate salts are unstable when dissolved in aqueous solutions. The fact that they decompose into elemental sulfur and sulfinates has been established (A. Westley and J. Westley, *Anal. Biochem.* 1984, 142, 163–166). This reaction is facile and, generally, a cloudy solution is visible within a short time of the dissolution of the thiosulfonate. Therefore, unless the entire solution of the thiosulfonate is used instantaneously, any unused solution will have to be discarded. This leads to waste and increased cost of producing the photographic material. Additionally, because the product of decomposition, elemental sulfur, is known to be photographically active (see EP 0 447,105; EP 0 297,804; EP 0 294,149 (AgCl); EP 0 327,272; EP 0 349,286; JP 2,161,423; JP 2,148,033; JP 2,148,031; JP 2,146,036; JP 2,033,141; JP 2,020,857; JP 2,301,744; JP 1,196,050; JP 1,196,034; DE 3,902,711; and U.S. Pat. No. 4,962,016), the presence of even a trace of elemental sulfur will cause unexpected and perhaps unwanted photographic responses. The instability of thiosulfonates has led to variability in the sensitized goods as well as increased cost in manufacturing the photographic materials. Thus there exists a need to overcome the disadvantage of the thiosulfonate salts in the process of manufacturing photographic materials containing such salts.

Compounds with labile sulfur moieties have been extensively used as sensitizers of silver halide emulsions. Their use and mechanism of action have been discussed in the photographic art such as by Pouradier, *J. Properties of Gelatin in Relation to Its Use in the Preparation of Photographic Emulsions*; James, T. H. Ed.; The Theory of the Photographic Process, 4th ed.; Macmillan: New York, 1977, Chapter 2; by Duffin, G. F. Photographic Emulsion Chemistry; Focal: London, 1966, Chapter 2 and by Mueller, F. W. H. in *The Photographic Emulsion*, Sturge, J. M. Ed.; Neblette's Handbook of Photographic and Reprography, 7th ed.; Van Nostrand Reinhold: New York, 1977, Chapter 2. Common among these labile sulfur compounds are thionates, thioureas, thiosulfates, isothiocyanates and sulfur containing amino acids such as cystine.

Thiatriazoles have been used as supersensitizers for silver halide photographic materials as described in U.S. Pat. No. 4,914,015 (substituted thia and oxa thiatriazoles in red and infrared spectrally sensitized emulsions); U.S. Pat. No. 4,780,404 (amino thiatriazoles); EP 0 447,647 (arylaminothiatriazoles substituted with at least one electron-withdrawing group); and JP 3,033,842 and JP 3,041,438, (thiatriazoles as supersensitizers in red sensitized silver halide emulsions). JP 63/037,348 describes using thiatriazoles in silver chloride emulsions to obtain a low D-min photographic material. JP 63/044,650 and JP 63/037,349 describe a high storage stability material. U.S. Pat. No. 5,070,008 describes using thiatriazoles in silver chloride emulsions with iridium and acidic conditions for formation of AgCl grains. JP 80/142,331 describes using a thiatriazole in a photothermographic paper to reduce fog. U.S. Pat. No. 5,006,448 describes using a thiatriazole as an inhibitor fragment that is released for improving interimage effects.

Pyrazolopentathiepins have been described as fungicides or as sulfur sensitizers in photographic emulsions in EP 0 138,622. In J62/299,963 thiepin is mentioned as an example of a class of compounds used for the preparation of silver halide emulsions which comprises at least 50 mol % of silver bromide.

U.S. Pat. No. 2,385,762 describes using a combination of diamino polysulfides and sulfinates or seleninates to stabilize silver halide emulsions. U.S. application Ser. No. 07/890,884 describes using diamino disulfides and monosulfinates to reduce the thermal sensitivity of high chlorides emulsions. U.S. Pat. No. 4,620,205 discloses the use of dithiodialkylamines as decolorizing agents in a two-color thermosensitive recording material. In JP 54/069,428 and JP 55/144,236 dithiodialkylamines are alleged to sensitize silver bromide emulsions.

There remains a continuing need for an effective means for heat stabilizing high chloride emulsions against thermal changes.

SUMMARY OF THE INVENTION

This invention provides a silver halide photographic element comprising a silver halide emulsion which is greater than 50 mole % silver chloride, said emulsion being in reactive association with a compound represented by Formula I $$MO_2S-Z-SO_2SM^1 \qquad (I)$$

wherein Z is a non-metallic arylene, alkylene, or heterocyclic group, and M and $M^1$ are independently cationic counter ions. It also provides a compound represented by Formula I.

It further provides a method of making a silver halide emulsion which is greater than 50 mole % silver chloride, comprising precipitating and chemically sensitizing the emulsion and further comprising adding to the emulsion a sulfur donating compound and a disulfinate compound represented by Formula II $$M^2O_2S-Z^1-SO_2M^3 \qquad (II)$$

wherein $Z^1$ is a non-metallic arylene, alkylene or heterocyclic group, and $M^2$ and $M^3$ are independently cationic counter ions.

The high chloride silver halide photographic elements of this invention exhibit very little variation in sensitivity upon changes in printing temperatures, while maintaining high resistance to storage changes. This allows for high quality prints without the need for constant readjustment of printing conditions during processing. Because of the presence of the sulfinate moiety in the thiosulfonate/sulfinate molecule, the ready decomposition observed for the non-sulfinate substituted thiosulfonate salts can be retarded or prevented.

DETAILED DESCRIPTION OF THE INVENTION

The thiosulfonate/sulfinate compounds of this invention are represented by Formula I $$MO_2S-Z-SO_2SM^1 \qquad (I)$$

Z is a substituted or unsubstituted alkylene, arylene, or heterocyclic group. Included in the definition of alkylene, arylene, or heterocyclic group are combinations of these groups. Preferably, the alkylene group contains 2 to 20 carbon atoms, with 1 to 10 carbon atoms being most preferred, and the arylene group contains 6 to 20 carbons atoms and more preferably 6 to 10 carbon atoms, with 6 carbon atoms being most preferred. The heterocyclic group may be a 5 to 15-membered ring containing one or two heteroatoms. More preferably, the heterocyclic group is a 5 or 6-membered ring. Preferred heteroatoms are nitrogen, oxygen, sulfur, selenium and tellurium, with nitrogen, oxygen, and sulfur being most preferred.

Examples of suitable arylene groups include phenylene, tolylene, naphthylene, and cycloheptatrienylene. Examples of suitable heterocyclic groups are pyrrole, furan, tetrahydrofuran, thiofuran, pyridine, picoline, piperidine, morpholine, pyrrolidine, thiophene, oxazole, thiazole, imidazole, selenazole, tellurazole, triazole, tetrazole and oxadiazole.

Substituents of Z may include, for example, alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups.

In the most preferred embodiment, Z is an arlyene group, and more particularly, an unsubstituted phenylene group or a phenylene group substituted in one or two positions.

M and $M^1$ are independently cationic counter ions and are preferably the same. More preferably, M and $M^1$ are alkali metal or ammonium ions, with sodium and potassium ions being most preferred.

Specific examples of formula (I) are shown below:

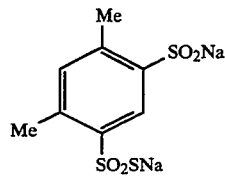   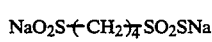

IA        IB

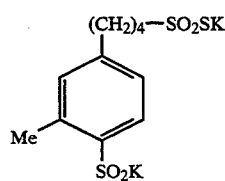

IC

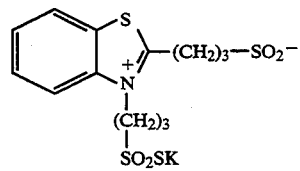

ID

The thiosulfonate/sulfinate compounds of this invention may be prepared by reacting the corresponding disulfinate compound with at least one compound from the class of materials known to donate sulfur.

The disulfinate compounds of this invention are represented by Formula (II):

$$M^2O_2S-Z^1-SO_2M^3$$

wherein $Z^1$, $M^2$ and $M^3$ are as defined above for Z, M and $M^1$, respectively. Specific examples of Formula (II) are shown below:

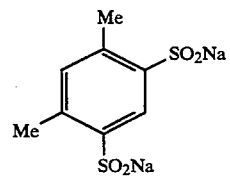   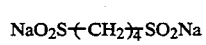

IIA        IIB

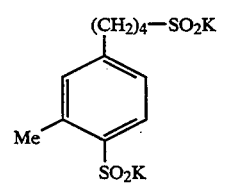

IIC

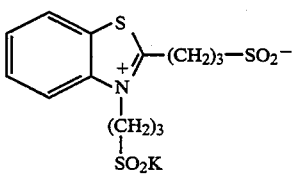

IID

The disulfinates are commercially available or they may be obtained by reduction of sulfonyl chlorides by methods known to those skilled in the art.

The sulfur donating compounds of this invention are those materials that extrude elemental sulfur on decomposition. Elemental sulfur is a form of sulfur that is zero valent and non-ionic. It is generally, but not always, expelled from the parent compound through a thermal process. That is, a myriad of other reactions, such as catalysis, and/or hydrolysis may take place, with the end result being that elemental sulfur is extruded from the parent molecule, sometimes known as the sulfur precursor. These compounds have been extensively reviewed in the published literature, see Loudon, J. D. *The Extrusion of Sulfur*, Kharasch, N. K. Ed. Organic Sulfur Compounds, Pergamon: Oxford, 1961, Vol. 1, p. 299; Stark, B. P. and Duke, A. J. *Extrusion Reactions*, Pergamon: Oxford, 1967, p. 91; Radl, S. Janssen Chim Acta, 1987, 5, 3; Guziec, F. S. Jr and Sanfilippo, L. J. Tetrahedron, 1988, 44, 6241 and in Williams, C. R. and Harpp, D. N. *Sulfur Reports*, 1990, 10 (2), 103–191. Many of these compounds release elemental sulfur near or slightly above room temperature while others require temperatures as high as 200° C. or above. Still others require, in addition to high heat, presence of a trace metal for catalysis of the extrusion reaction. The preferred compounds of this invention are the ones that do not require a high temperature for extrusion, nor a specific catalyst or solvent, even though a catalytic reaction may take place in the silver halide emulsion to facilitate the extrusion reaction. More preferable are the compounds that will extrude sulfur below 200° C., and are stable at room temperature.

Examples of such sulfur donating compounds are certain disulfides, polysulfides, bis-alkylamino disulfides, sulfenic sulfonic thioanhydrides, thiosulfonate salts, aminothiosulfonates, acylmethylmercapto azoles or azolium salts, thiazepines, thiepins, 1,4-dithiins, 1,2-, 1,3-, or 1,4-thiazines, 1,4,2-dithiazines, 1,3,4-, 1,2,6-, 1,3,5-thiadiazines, dihydro derivatives of dithiazines or thiadiazines, and 1,2,3,4-thiatriazoles. Vulcanizing agents such as those discussed by Porter, M. in *Vulcanization* of Rubber; Oae, S. Ed.; Organic Chemistry of Sulfur; Plenum: New York, 1977, Chapter 3, and by Hofmann, W. *Vulcanization and Vulcanizing Agents*; Palmerton: New York, 1967 may also be effective. They include thiuram tetrasulfides, benzothiazolyl-2-N-dithiomorpholide, and di-morpholino disulfide. Elemental sulfur when appropriately dissolved in alcoholic solvents may also be useful. The following classes of sulfur donating compounds are particularly useful.

The acylmethylmercapto azolium salts are represented by Formula (A)

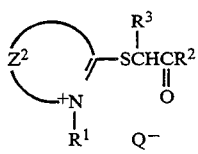

(A)

In the above structure $Z^2$ contains the atoms necessary to form either a 5 or 6-membered fused or non-fused heterocyclic ring. Preferred heteroatoms are nitrogen, oxygen and sulfur. Examples of suitable heterocyclic groups are pyrrole, pyridine, picoline, piperidine, morpholine, pyrrolidine, oxazole, thiazole, imidazole, triazole, tetrazole, and oxadiazole. $R^1$ and $R^2$ are substituted or unsubstituted alkyl or aryl groups, more preferably they are alkyl groups having 1 to 20 carbon atoms, with 1 to 6 carbon atoms being most preferred, or aryl groups having 6 to 10 carbons atoms, with 6 carbon atoms being most preferred. Examples of suitable substituents include alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups. Preferred are simple alkyl groups.

$R^3$ is H, or an alkyl or aryl group as described for $R^1$ and $R^2$ and each may be further substituted as described for $R^1$ and $R^2$. Q is an anion which may be, for example, a halide, a perchlorate, a hexafluorophosphate, a tetrafluoroborate, an organic carboxylate or a sulfonate. Examples of these of salts are shown below:

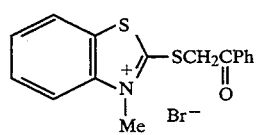

A1

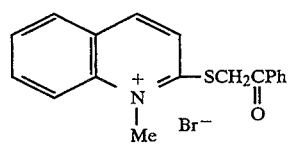

A2

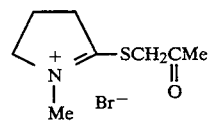

A3

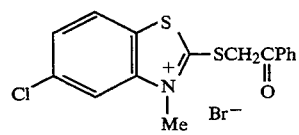

A4

The thiepins are represented by Formula (B).

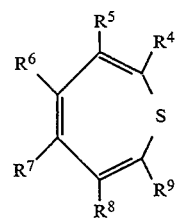

(B)

$R^4$, $R^5$, $R^6$, $R^7$, $R^8$, and $R^9$ are independently H or substituted or unsubstituted alkyl or aryl groups. $R^4$, $R^5$, $R^6$, $R^7$, $R^8$, and $R^9$ together may form fused rings. Preferably, the alkyl groups contain 1 to 20 carbon atoms, with 1 to 6 carbon atoms being most preferred, and the aryl groups contain 6 to 10 carbons atoms, with 6 carbon atoms being most preferred. Examples of suitable substituents include alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups. Preferred are carboxy groups.

Examples of specific thiepin compounds are shown below.

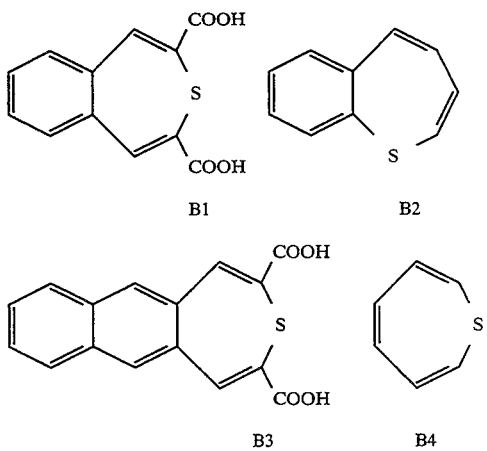

B1    B2

B3    B4

The 1,2,3,4-thiatriazoles are represented by Formula (C) below.

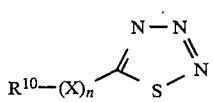

(C)

$R^{10}$ is a substituted or unsubstituted alkyl or aryl group, more preferably an alkyl group having 1 to 20 carbon atoms, with 1 to 6 carbon atoms being most preferred, or an aryl group having 6 to 10 carbon atoms, with 6 carbon atoms being most preferred. Examples of suitable substituents include alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups. Preferred are hydroxy groups.

n may be 0 or 1. When n is 1, X is a heteroatom such as N, O or S. When the linking atom is N, there may be further substitution on the N such as described above for $R^{10}$. Specific examples of 1,2,3,4-thiatriazoles are shown below.

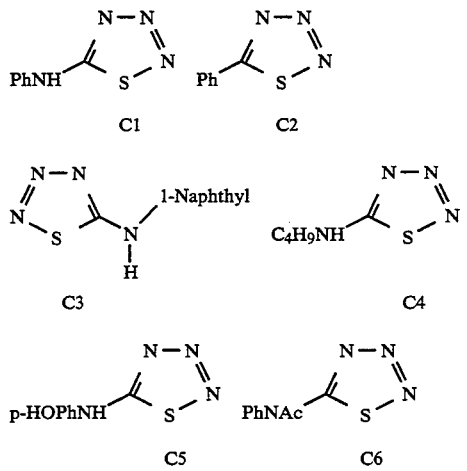

The aryldialkylamino disulfides are represented by Formula (D) below.

$ArSSNR^{11}R^{12}$      (D)

In Formula (D), one sulfur atom is bonded directly to a nitrogen atom and the other sulfur atom is bonded to a carbon atom which is part of an aromatic or heteroaromatic ring, Ar. When Ar is an aromatic group, it may be either a single ring or a condensed ring, preferably having 6 to 10 carbon atoms, and more preferably, having 6 carbon atoms. Examples of suitable aromatic groups include phenyl, tolyl, naphthyl, and cycloheptatrienyl. When Ar is a heteroaromatic ring it may include, for example, pyrrole, pyridine, thiophene, quinoline, benzofuran, pyrazole, oxadiazole, thiadiazole, triazole, tetrazole, benzoxazole, benzothiazole, benzimidazole, or benzotriazole ring systems.

Ar may be further substituted or may be unsubstituted. Examples of suitable substituents include alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups. Preferred are alkyl groups.

$R^{11}$ and $R^{12}$ are alkyl groups, or together they may form a ring. Examples of such rings include morpholine, piperidine, pyrazolidine, pyrrolidine, and imidazolidine rings. Preferably, the alkyl groups contain 1 to 20 carbon atoms, with 1 to 10 carbon atoms being most preferred. $R^{11}$ and $R^{12}$ may be substituted as described for Ar.

Specific examples of aryldialkylamino disulfides are shown below.

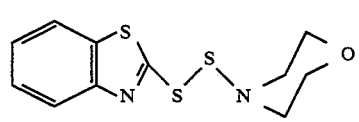

D1

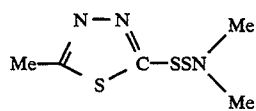

D2

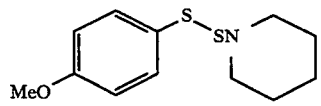

D3

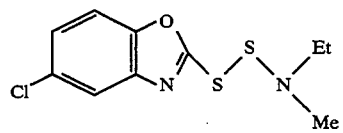

D4

The thiosulfonate salts are represented by Formula (E) below.

$R^{13}SO_2SM$      (E)

$R^{13}$ is a substituted or unsubstituted alkyl, aryl, or heterocyclic group. Preferably, the alkyl groups contain 1 to 20 carbon atoms, with 1 to 10 carbon atoms being most preferred, and the aryl groups contain 6 to 10 carbon atoms, with 6 carbon atoms being most preferred. The heterocyclic group may be a 5 to 15-membered ring containing one or two heteroatoms. Preferred hetero atoms are nitrogen, sulfur and oxygen. More preferably, the heterocyclic group is a 5 or 6-membered ring. Examples of suitable aryl groups include phenyl, tolyl, naphthyl, and cycloheptatrienyl. Examples of suitable heterocyclic rings are pyrrole, furan, tetrahydrofuran, thiofuran, pyridine, picoline, piperidine, morpholine, pyrrolidine, thiophene, oxazole, thiazole, imidazole, triazole, tetrazole and oxadiazole. Preferably, $R^{13}$ is an unsubstituted phenyl group or a phenyl group substituted in one or two 5 positions. Such substituents of $R^{13}$ may include, for example, alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups. Preferred are alkyl or alkoxy groups. M is a cationic counter ion that may be an alkali metal or an ammonium ion.

Specific examples of thiosulfonate salts are illustrated below:

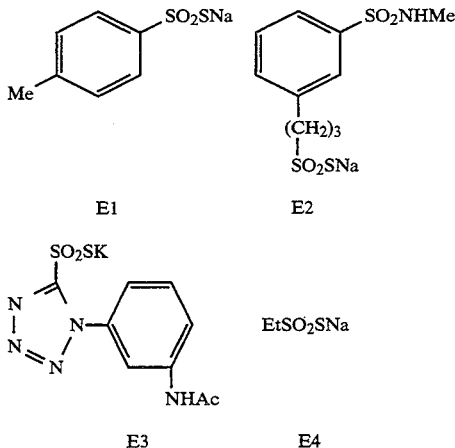

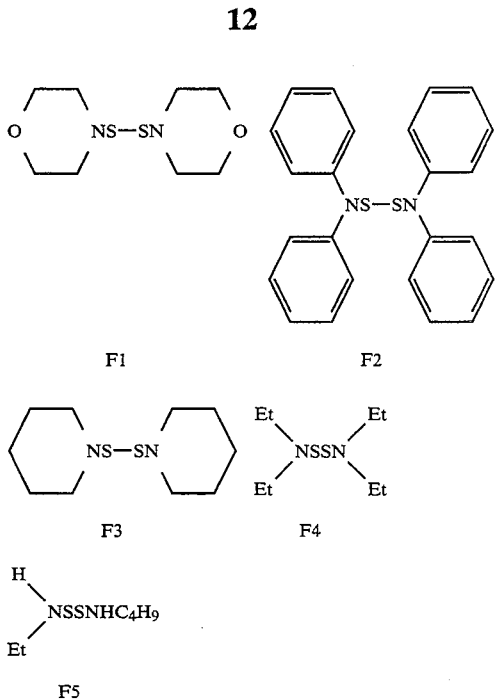

The diamino disulfides (also known as dithioamines) are represented by Formula (F) shown below.

$R^{14}R^{15}NSSNR^{16}R^{17}$  (F)

Each of the sulfur atoms of Formula (F) is bonded to each other and directly to a nitrogen atom. $R^{14}$, $R^{15}$, $R^{16}$, $R^{17}$ independently are hydrogen, or an alkyl, aryl, or heterocycle group or $R^{14}$, $R^{15}$, $R^{16}$, $R^{17}$ may form part of a ring system which may incorporate atoms such as S, O, or N. Examples of such ring systems include piperidine, morpholine, pyrrolidine and imidazolidine. Preferably, the alkyl groups contain 1 to 20 carbon atoms, with 1 to 10 carbon being most preferred, and the aryl groups contain 6 to 10 carbons atoms, with 6 carbon atoms being most preferred. The heterocyclic group may be a 5 to 15-membered ring containing one or two heteroatoms. The preferred heteroatoms are oxygen, nitrogen and sulfur. More preferably, the heterocyclic group is a 5 or 6-membered ring. Examples of suitable aryl groups include phenyl, tolyl, naphthyl, and cycloheptatrienyl. Examples of suitable heterocyclic groups are pyrrole, furan, tetrahydrofuran, thiofuran, pyridine, pyrrolidine, thiophene, oxazole, thiazole, imidazole, selenazole, tellurazole, triazole, tetrazole and oxadiazole.

Substituents of $R^{14}$, $R^{15}$, $R^{16}$, $R^{17}$ may include, for example, alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups. Preferred are alkyl groups.

Specific examples of diaminodisulfides are illustrated below.

The preparation of these sulfur donors are known to those skilled in the art and many of them are commercially available.

The thiosulfonate/sulfinate compound may be prepared by mixing a sulfur donating compound in a solvent such as methanol or tetrahydrofuran with an excess amount of disulfinic acid. Depending on the sulfur donor, the mixture is stirred at room temperature or slightly above. The solvent is evaporated at the end of the reaction and the product is purified by repeated recrystallization, distillation or chromatography.

Because of the difficulty in obtaining completely pure compounds, the prior preparation or isolation of the thiosulfonate/sulfinate compound is not preferred. A more preferred and simpler method of preparing these compounds is to generate them in situ in the emulsion by adding the disulfinate and the sulfur donating compound directly to a silver halide emulsion.

The concentration of sulfur donors and disulfinate compounds which may be utilized covers a wide range. Because of the variety of structures of the sulfur donors and the disulfinate compounds, the levels used will be dependent on the timing of the addition, the layer to which the compounds are added, the type of emulsion and other variables. Those skilled in the art will realize that the balance of the sulfur donor and the disulfinate compound needed to achieve optimal heat stability and antifogging will vary depending on the desired final product. Generally, the useful concentrations of the sulfur donor are from $10^{-5}$ to 10 g/mol silver, more preferably from $10^{-4}$ to 5 g/mol silver, and most preferably from $10^{-3}$ to 1 g/mol silver. Useful concentrations of the disulfinate compound are from $10^{-4}$ to 100 g/mol silver, more preferably from $10^{-3}$ to 50 g/mol silver, and most preferably from $10^{-2}$ to 10 g/mol silver. The disulfinate is always added in excess relative to the sulfur donor. Thus the ratio of disulfinate to the sulfur donor may be anywhere between 1:1 up to 10:1.

The sulfur donors and disulfinate compounds may be added to the photographic emulsion using any technique suitable for this purpose. If the sulfur donors or disulfinate compounds are hydrophobic, they may be dissolved in any common organic solvent such as methanol or a mixed aqueous methanolic solution. Examples of other suitable solvents or diluents include ethanol, or acetone. If the sulfur donors or disulfinate compounds are water soluble they can be premixed or they can be added separately in aqueous solutions directly to the emulsion. The sulfur donors and disulfinate compounds can be added to the emulsion in the form of a liquid/liquid dispersion similar to the technique used with certain couplers. They can also be added as a solid particle dispersion.

The sulfur donor and disulfinate compound may be added to any layer where they are in reactive association with the silver chloride. By "in reactive association with" it is meant that the sulfur donor and the disulfinate compound must be contained in the silver chloride emulsion layer or in a layer whereby they can react or interreact with the silver chloride emulsion. For example, they can also be added to gelatin-only overcoats or interlayers, or to water-only overcoats.

The combination of disulfinates and sulfur donor may be used in addition to any conventional emulsion stabilizer or antifoggant as commonly practiced in the art. Combinations of more than one sulfur donor or disulfinate compound may be utilized.

The photographic emulsions of this invention are generally prepared by precipitating silver halide crystals in a colloidal matrix by methods conventional in the art. The colloid is typically a hydrophilic film forming agent such as gelatin, alginic acid, or derivatives thereof.

The crystals formed in the precipitation step are chemically and spectrally sensitized, as known in the art. Chemical sensitization of the emulsion employs sensitizers such as sulfur-containing compounds, e.g., allyl isothiocyanate, sodium thiosulfate and allyl thiourea; reducing agents, e.g., polyamines and stannous salts; noble metal compounds, e.g., gold, platinum; and polymeric agents, e.g., polyalkylene oxides. A temperature rise is employed to complete chemical sensitization (heat treatment). Spectral sensitization is effected with agents such as sensitizing dyes. For color emulsions, dyes are added in the spectral sensitization step using any of a multitude of agents described in the art. It is known to add such dyes both before and after heat treatment.

After spectral sensitization, the emulsion is coated on a support. Various coating techniques include dip coating, air knife coating, curtain coating and extrusion coating.

The sulfur donors and disulfinate compounds of this invention may be added to the silver halide emulsion at any time during the preparation of the emulsion, i.e., during precipitation, during or before chemical sensitization or during final melting and comixing of the emulsion and additives for coating. Most preferably these compounds are added after chemical sensitization. The sulfur donor and the disulfinate compound do not have to added simultaneously, and they may be added at different points in the preparation of the emulsion. Preferably the disulfinate compound is added first followed by the sulfur donor.

The photographic elements of this invention can be any photographic recording material comprising, at least one high chloride silver emulsion. The other emulsions of the photographic element may have any halide content. For example, the photographic element may also contain silver bromide or silver iodobromide emulsions. The silver chloride emulsion must be comprised of greater than 50 mole percent, and more preferably, greater than 90 mole percent silver chloride.

The photographic elements of this invention can be non-chromogenic silver image forming elements. They can be single color elements or multicolor elements. Multicolor elements typically contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described in Whitmore U.S. Pat. No. 4,362,806 issued Dec. 7, 1982. The element can contain additional layers such as filter layers, interlayers, overcoat layers, subbing layers and the like. This invention may be particularly useful with those photographic elements containing a magnetic backing such as described in No. 34390, *Research Disclosure*, November, 1992.

In the following discussion of suitable materials for use in the emulsions and elements of this invention, reference will be made to *Research Disclosure*, Dec. 1989, Item 308119, published by Kenneth Mason Publications, Ltd., Dudley Annex, 12a North Street, Emsworth, Hampshire P010 7DQ, ENGLAND, the disclosures of which are incorporated herein by reference. This publication will be identified hereafter by the term "Research Disclosure".

The silver halide emulsions employed in the elements of this invention can be either negative-working or positive-working. Examples of suitable emulsions and their preparation are described in Research Disclosure Sections I and II and the publications cited therein. Other suitable emulsions are (111) tabular silver chloride emulsions such as described in U.S. Pat. Nos. 5,176,991 (Jones et al); 5,176,992 (Maskasky et al); 5,178,997 (Maskasky); 5,178,998 (Maskasky et al); 5,183,732 (Maskasky); and 5,185,239 (Maskasky) and (100) tabular silver chloride emulsions such as described in EP 0 534,395, published Mar. 31, 1993 (Brust et al). Some of the suitable vehicles for the emulsion layers and other layers of elements of this invention are described in Research Disclosure Section IX and the publications cited therein.

The silver halide emulsions can be chemically and spectrally sensitized in a variety of ways, examples of which are described in Sections III and IV of the Research Disclosure. The elements of this invention can include various dye-forming couplers including but not limited to those described in Research Disclosure Section VII, paragraphs D, E, F and G and the publications cited therein. These couplers can be incorporated in the elements and emulsions as described in Research Disclosure Section VII, paragraph C and the publications cited therein.

The photographic elements of this invention or individual layers thereof can contain, among other things, brighteners (Examples in Research Disclosure Section V), antifoggants and stabilizers (Examples in Research Disclosure Section VI), antistain agents and image dye stabilizers (Examples in Research Disclosure Section VII, paragraphs I and J), light absorbing and scattering materials (Examples in Research Disclosure Section VIII), hardeners (Examples in Research Disclosure Section X), plasticizers and lubricants (Examples in Research Disclosure Section XII), antistatic agents (Examples in Research Disclosure Section XIII), matting agents (Examples in Research Disclosure Section XVI) and development modifiers (Examples in Research Disclosure Section XXI).

The photographic elements can be coated on a variety of supports including but not limited to those described in Research Disclosure Section XVII and the references described therein.

Photographic elements can be exposed to actinic radiation, typically in the visible region of the spectrum, to form a latent image as described in Research Disclosure Section XVIII and then processed to form a visible dye image examples of which are described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide elements, the processing step described above gives a negative image. To obtain a positive (or reversal) image, this step can be preceded by development with a non-chromogenic developing agent to develop exposed silver halide, but not form dye, and then uniformly fogging the element to render unexposed silver halide developable, and then developed with a color developer. Additionally, the preceding process can be employed but before uniformly fogging the emulsion the remaining silver halide is dissolved and the developed silver is converted back to silver halide; the conventional E-6 process is then continued and results in a negative color image. Alternatively, a direct positive emulsion can be employed to obtain a positive image.

Development is followed by the conventional steps of bleaching, fixing, or bleach-fixing, to remove silver and silver halide, washing and drying.

The following examples are intended to illustrate, without limiting, this invention.

EXAMPLES

Example 1

A chemically and blue spectrally sensitized monodisperse silver chloride negative emulsion containing yellow dye-forming coupler α-(4-(4-benzyloxy-phenyl-sulfonyl)phenoxy)-α(pivalyl)-2-chloro-5-(γ-(2,4-di-5-amylphenoxy)butyramido)acetanilide (1.08 g/m$^2$) in di-n-butylphthalate coupler solvent (0.27 g/m$^2$) and gelatin (1.51 g/m$^2$) was prepared. In addition, 0.104 g of 1-(3-acetamidophenyl)-5-mercaptotetrazole and 1.033 g of potassium bromide per silver mole were added. The emulsion was divided and various concentrations of a methanolic solution of the disulfide F1 and the disulfinate, IIA were added to the different portions. The emulsions (0.34 g Ag/m$^2$) were coated on a resin coated paper support and a 1.076 g/m$^2$ gel overcoat was applied as a protective layer along with the hardener bis (vinylsulfonyl) methyl ether in an amount of 1.8% of the total gelatin weight. The emulsions were then stored at 0° F. and 120° F. for one and two weeks.

The coatings were given a 0.1 second exposure, using a 0–3 step tablet (0.15 increments) with a tungsten lamp designed to simulate a color negative print exposure source. This lamp had a color temperature of 3000K, log lux 2.95, and the coatings were exposed through a combination of magenta and cyan filters, a 0.3 ND (Neutral Density), and a UV filter. The processing consisted of color development (45 sec, 35° C.), bleach-fix (45 sec, 35° C.) and stabilization or water wash (90 sec, 35° C.) followed by drying (60 sec, 60° C.). The chemistry used in the Colenta processor consisted of the following solutions:

| Developer: | |
|---|---|
| Lithium salt of sulfonated polystyrene | 0.25 mL |
| Triethanolamine | 11.0 mL |
| N,N-diethylhydroxylamine (85% by wt.) | 6.0 mL |
| Potassium sulfite (45% by wt.) | 0.5 mL |
| Color developing agent (4-(N-ethyl-N-2-methanesulfonyl aminoethyl)-2-methyl-phenylenediaminesesquisulfate monohydrate | 5.0 g |
| Stilbene compound stain reducing agent | 2.3 g |
| Lithium sulfate | 2.7 g |
| Acetic acid | 9.0 mL |
| Water to total 1 liter, pH adjusted to 6.2 | |
| Potassium chloride | 2.3 g |
| Potassium bromide | 0.025 g |
| Sequestering agent | 0.8 mL |
| Potassium carbonate | 25.0 g |
| Water to total of 1 liter, pH adjusted to 10.12 | |
| Bleach-fix | |
| Ammonium sulfite | 58 g |
| Sodium thiosulfate | 8.7 g |
| Ethylenediaminetetraacetic acid ferric ammonium salt | 40 g |
| Stabilizer | |
| Sodium citrate | 1 g |
| Water to total 1 liter, pH adjusted to 7.2 | |

The speed at 1.0 density unit was taken as a measure of the sensitivity of the emulsion. Heat sensitivity data was obtained on a sensitometer which was modified with a water jacket so that the temperature of the step tablet could be maintained at 22° C. or increased to 40° C. A 0.1 second exposure was made with a 3000883 K light source and the coatings were processed using standard color paper processing, KODAK'S PROCESS RA-4. The change in speed due to the temperature variation (Δspeed) was calculated at the 1.0 density point of the D log E curve and is shown in Table 1.

Table I also illustrates the changes in fog (Δfog) after storage for 1 and 2 weeks at 0° F. and 120° F. and 50% relative humidity.

TABLE I

| F1 mg Ag mole | IIA | Sample # | 1 week 120° F. vs 0° F. ΔFog | 2 week 120° F. vs 0° F. ΔFog | Heat Sensitivity 40° C. vs 22° C. ΔSpeed |
|---|---|---|---|---|---|
| 0 | 0 | 1 (comparison) | 0.27 | 0.70 | 3 |
| 0 | 1360 | 2 (comparison) | 0.30 | 0.80 | 2 |
| 47 | 0 | 3 (comparison) | 0.09 | 0.25 | −11 |
| 47 | 470 | 4 (invention) | 0.14 | 0.32 | 3 |
| 71 | 710 | 5 (invention) | 0.13 | 0.29 | 0 |
| 94 | 940 | 6 (invention) | 0.12 | 0.26 | 1 |

It can be seen that the coatings containing F1 have smaller fog growth from storage than the control (samples 3, 4, 5, and 6 relative to sample 1). The coating with only F1 (sample 3) causes the heat sensitivity change to go negative, an undesirable position. However, certain coatings with the combination of F1 and IIA (samples 5, and 6) have smaller changes in heat sensitivity but still reduce fog growth. Note that IIA alone in the coating (sample 2) has little effect on either the keeping or the heat sensitivity properties of the emulsion.

Example 2

In this example, the beneficial effect of the combination of F1 and IIA is seen in a red sensitized emulsion. This emulsion was prepared as in Example 1 except the emulsion was coated at 0.18 g Ag/m$^2$, and the cyan dye-forming coupler 2-($\alpha$(2,4-di-tert-amyl-phenoxy)-butyramido)-4,6-dichloro-5-ethyl phenol (0.42 g/m$^2$) in di-n-butyl phthalate coupler solvent (0,429 g/m$^2$) and gelatin (1.08 g/m$^2$) were used. The amount of 1-(3-acetamidophenyl)-5-mercaptotetrazole and potassium bromide were changed to 0.38 and 1.1 g per silver mole, respectively. The emulsions were stored at 0° F. and 120° F. for 1 and 2 weeks and then exposed and processed as described above. The data in Table II show the changes in fog ($\Delta$fog) and heat sensitivity.

TABLE II

| F1 mg Ag mole | IIA | Sample # | 1 week 120° F. vs 0° F. $\Delta$Fog | 2 week 120° F. vs 0° F. $\Delta$Fog | Heat Sensitivity 40° C. vs 22° C. $\Delta$Speed |
|---|---|---|---|---|---|
| 0 | 0 | 7 (comparison) | 0.26 | 0.52 | 9 |
| 0 | 950 | 8 (comparison) | 0.24 | 0.53 | 8 |
| 118 | 0 | 9 (comparison) | 0.04 | 0.06 | −6 |
| 118 | 118 | 10 (invention) | 0.01 | 0.03 | −4 |
| 118 | 590 | 11 (invention) | 0.00 | 0.02 | −1 |

It can be seen that all the coatings with F1 (samples 9–11) reduce fog growth but that the heat sensitivity has turned negative relative to the control (sample 7). However, a combination of F1 and IIA (e.g. sample 11) imparts a smaller speed change than either the control or F1 alone and still effectively reduces fog growth.

Example 3

In this experiment a silver halide emulsion was prepared as described in Example 1 except that the combination of thiosulfonate E1 and IIA was added. The emulsions were stored at 0° F. and 120° F. for 1 and 2 weeks and then exposed and processed as described above. The data in Table III shows the changes in fog ($\Delta$fog) and heat sensitivity.

TABLE III

| E1 mg Ag mole | IIA | Sample # | 1 week 120° F. vs 0° F. $\Delta$Fog | 2 week 120° F. vs 0° F. $\Delta$Fog | Heat Sensitivity 40° C. vs 22° C. $\Delta$Speed |
|---|---|---|---|---|---|
| 0 | 0 | 1 (comparison) | 0.27 | 0.70 | 3 |
| 0 | 1360 | 2 (comparison) | 0.30 | 0.80 | 2 |
| 91 | 0 | 12 (comparison) | 0.16 | 0.38 | 2 |
| 91 | 910 | 13 (invention) | 0.13 | 0.34 | 0 |
| 114 | 1140 | 14 (invention) | 0.13 | 0.35 | 2 |
| 136 | 1360 | 15 (invention) | 0.12 | 0.31 | 2 |

It can be seen from Table III that E1 reduces the fog growth of coatings during incubation (samples 12–15) to nearly half of the control sample (sample 1). A combination of E1 and IIA (sample 13), however, reduces the speed change from heat sensitivity to zero and still maintains the antifogging property of E1 alone.

Example 4

In this example, the beneficial effect of the combination of IIA and B1 is seen in a blue sensitized emulsion prepared as in Example 1. The emulsions were stored at 0° F. and 120° F. for 1 and 2 weeks and then exposed and processed as described above. The data in Table IV shows the changes in fog ($\Delta$fog) and heat sensitivity.

TABLE IV

| B1 mg Ag mole | IIA | Sample # | 1 week 120° F. vs 0° F. $\Delta$Fog | 2 week 120° F. vs 0° F. $\Delta$Fog | Heat Sensitivity 40° C. vs 22° C. $\Delta$Speed |
|---|---|---|---|---|---|
| 0 | 0 | 1 (comparison) | 0.27 | 0.70 | 3 |
| 0 | 1360 | 2 (comparison) | 0.30 | 0.80 | 2 |
| 50 | 0 | 16 (comparison) | 0.02 | 0.22 | −27 |
| 50 | 500 | 17 (invention) | 0.13 | 0.35 | −1 |
| 75 | 750 | 18 (invention) | 0.09 | 0.27 | −2 |
| 100 | 1000 | 19 (invention) | 0.07 | 0.24 | −2 |

It can be seen from Table IV that the coatings containing the combination of IIA and B1, (samples 17, 18 and 19) have a smaller fog increase and smaller speed change when exposed at high temperature than the control (sample 1) which has none of the compounds of the present invention. The coating with only B1 (sample 16) shows suppressed fog growth, but the heat sensitivity has an undesirable negative change.

Example 5

This example shows the effect of the combination of IIA and B1 in a red sensitized emulsion prepared as described in example 2. The emulsions were stored at 0° F. and 120° F for 1 and 2 weeks and then exposed and processed as described above. The data in Table V shows the changes in fog ($\Delta$fog) and heat sensitivity.

TABLE V

| B1 mg Ag mole | IIA | Sample # | 1 week 120° F. vs 0° F. $\Delta$Fog | 2 week 120° F. vs 0° F. $\Delta$Fog | Heat Sensitivity 40° C. vs 22° C. $\Delta$Speed |
|---|---|---|---|---|---|
| 0 | 0 | 7 (comparison) | 0.26 | 0.52 | 9 |
| 0 | 950 | 8 (comparison) | 0.24 | 0.53 | 8 |
| 124 | 0 | 20 (comparison) | 0.01 | 0.09 | −18 |
| 124 | 124 | 21 (invention) | 0.01 | 0.05 | −1 |
| 124 | 620 | 22 (invention) | 0.01 | 0.06 | 3 |

All of the coatings containing B1 (samples 20–22) show significantly lower fog growth than the coatings without B1. Upon exposure at high temperature, the control coating (sample 7) shows increased speed, but the coating containing B1 alone shows significantly decreased speed (sample 20). However, samples 21 and 22 with both IIA and B1 show the least amount of speed change and low fog growth.

Example 6

In this example, the beneficial effect of the combination of A1 and IIA is seen in a red sensitized emulsion prepared as described in Example 2. The emulsions were stored at 0° F. and 140° F. for 1 week and 0° F. and 120° F. for 2 weeks and then exposed and processed as described above. The data in Table VI shows the changes in fog ($\Delta$fog) and heat sensitivity.

TABLE VI

| A1 mg Ag mole | IIA | Sample # | 1 week 140° F. vs 0° F. $\Delta$Fog | 2 week 120° F. vs 0° F. $\Delta$Fog | Heat Sensitivity 40° C. vs 22° C. $\Delta$Speed |
|---|---|---|---|---|---|
| 0 | 0 | 23 (comparison) | 0.15 | 0.07 | 7 |
| 0 | 150 | 24 (comparison) | 0.14 | 0.05 | 6 |

TABLE VI-continued

| A1 mg Ag mole | IIA | Sample # | 1 week 140° F. vs 0° F. ΔFog | 2 week 120° F. vs 0° F. ΔFog | Heat Sensitivity 40° C. vs 22° C. ΔSpeed |
|---|---|---|---|---|---|
| 5 | 0 | 25 (comparison) | 0.12 | 0.05 | 2 |
| 5 | 50 | 26 (invention) | 0.10 | 0.05 | 3 |
| 15 | 0 | 27 (comparison) | 0.07 | 0.03 | −5 |
| 15 | 150 | 28 (invention) | 0.06 | 0.04 | 0 |

Table VI shows the reduction in heat sensitivity for coatings containing A1 (samples 25-28) relative to the two coatings without (samples 23, and 24). Sample 28, the coating with both A1 and IIA shows no change in speed upon exposure at elevated temperature relative to the control and very little fog growth.

Example 7

This example shows that the combination of sulfinates and the sulfur donor can be added during the sensitization step of the emulsion. In a red spectrally sensitized emulsion similar to that used in example 2, 1-(3-acetamidophenyl)-5-mercaptotetrazole (S), IIA, or IIB and F1 were added to the emulsion at 65° C. and then digested for 28 minutes. The emulsion was then coated as described in Example 2. The emulsions were stored at 0° F. and 120° F. for 1 and 2 weeks and then exposed and processed as described above. The data in Table VII shows the changes in fog (Δfog) and heat sensitivity.

TABLE VII

| S mg Ag mole | F1 | II | Sample # | 1 week 120° F. vs 0° F. ΔFog | 2 week 120° F. vs 0° F. ΔFog | Heat Sensitivity 40° C. vs 22° C. ΔSpeed |
|---|---|---|---|---|---|---|
| 247 | 0 | 0 | 29 (comparison) | 0.32 | 0.52 | 13 |
| 247 | 40 | IIA | 30 (invention) | 0.02 | 0.03 | −4 |
| 247 | 40 | IIB | 31 (invention) | 0.05 | 0.08 | 5 |
| 257 | 0 | 0 | 32 (comparison) | 0.13 | 0.25 | 10 |
| 257 | 40 | IIA | 33 (invention) | 0.01 | 0.03 | −2 |
| 257 | 40 | IIB | 34 (invention) | 0.03 | 0.06 | 6 |
| 267 | 0 | 0 | 35 (comparison) | 0.15 | 0.26 | 11 |
| 267 | 40 | IIA | 36 (invention) | 0.01 | 0.03 | −1 |
| 267 | 40 | IIB | 37 (invention) | 0.03 | 0.04 | 5 |
| 277 | 0 | 0 | 38 (comparison) | 0.13 | 0.25 | 10 |
| 277 | 20 | IIA | 39 (invention) | 0.03 | 0.04 | 3 |
| 277 | 20 | IIB | 40 (invention) | 0.07 | 0.13 | 8 |
| 287 | 0 | 0 | 41 (comparison) | 0.08 | 0.17 | 10 |
| 287 | 20 | IIA | 42 (invention) | 0.03 | 0.04 | 4 |
| 287 | 20 | IIB | 43 (invention) | 0.04 | 0.07 | 8 |
| 297 | 0 | 0 | 44 (comparison) | 0.05 | 0.08 | 9 |
| 297 | 20 | IIA | 45 (invention) | 0.02 | 0.04 | 3 |
| 297 | 20 | IIB | 46 (invention) | 0.03 | 0.07 | 8 |
| 297 | 0 | IIA | 47 (comparison) | 0.05 | 0.08 | 8 |
| 297 | 0 | IIB | 48 (comparison) | 0.06 | 0.11 | 9 |
| 267 | 40 | 0 | 49 (comparison) | 0.26 | 0.57 | 1 |
| 297 | 20 | 0 | 50 (comparison) | 0.12 | 0.27 | 0 |

IIA and IIB are added at 10× weight of D1 for each coating except for samples 47 and 48 where they are added at 400 mg/Ag mol.

For each level of compound S, the heat sensitivity of the inventive emulsions is lower than that of the comparison without F1 and II while still maintaining a lower fog position. While the combination of S with F1 appears to reduce heat sensitivity (samples 49 and 50), the level of fog is actually higher than the corresponding coatings with the same level of S but without F1 (samples 35 and 44). Additionally, the coatings with only S and II (samples 47 and 48) show no improvement in heat sensitivity relative to the coatings with the same level of S but without II. Thus, depending on the level of S, F1 and II, an emulsion can be obtained such that there is a minimum change in fog and a high resistance to temperature sensitivity during exposure (e.g. sample 36).

In summary, the keeping and the heat sensitivity properties of silver chloride emulsions can clearly be modified by the presence of a thiosulfonate/sulfinate compound. Depending on the levels of these materials used, the ratio of sulfur donors to disulfinates and the nature of the sulfur precursors, those skilled in the art can optimize each of these parameters to best suit the needs of the photographic emulsions and applications.

While the invention has been described in detail and with reference to specific embodiments thereof, it will be apparent to one skilled in the art that various changes and modifications can be made therein without departing from the spirit and scope thereof.

What is claimed is:

1. A silver halide photographic element comprising a silver halide emulsion which is greater than 50 mole % silver chloride, said emulsion being in reactive association with a compound represented by Formula I $$MO_2S-Z-SO_2SM^1 \qquad (I)$$

wherein Z is a non-metallic arylene, alkylene or heterocyclic group, and M and $M^1$ are independently cationic counter ions.

2. The photographic element of claim 1 wherein Z is an alkylene group of 1 to 20 carbon atoms, an arylene group of 6 to 20 carbon atoms or a heterocyclic group of 5 to 15 members with at least one atom selected from nitrogen, oxygen, sulfur, selenium and tellurium, and M and $M^1$ are alkali metal or ammonium ions.

3. The photographic element of claim 2 wherein Z is an alkylene group of 1 to 10 carbon atoms, an arylene group of 6 to 10 carbon atoms or a heterocyclic group of 5 to 6 members with at least one atom selected from nitrogen, oxygen, and sulfur, and M and $M^1$ are alkali metal ions.

4. The photographic element of claim 3 wherein Z is an arylene group, and M and $M^1$ are sodium or potassium.

5. The photographic element of claim 1 wherein the silver halide emulsion is greater than 90 mole % silver chloride.

6. A method of making a silver halide emulsion which is greater than 50 mole % silver chloride, comprising precipitating and chemically sensitizing the emulsion and further comprising adding to the emulsion a sulfur donating compound and a disulfinate compound represented by Formula II $$M^2O_2S-Z^1-SO_2M^3 \qquad (II)$$

wherein $Z^1$ is a non-metallic arylene, alkylene or heterocyclic group, and $M^2$ and $M^3$ are independently cationic counter ions.

7. The method of claim 6 wherein $Z^1$ is an alkylene group of 1 to 20 carbon atoms, an arylene group of 6 to 20 carbon atoms or a heterocyclic group of 5 to 15 members with at least one atom selected from nitrogen, oxygen, sulfur, selenium and tellurium, and $M^2$ and $M^3$ are alkali metal or ammonium ions.

8. The method of claim 7 wherein $Z^1$ is an alkylene group of 1 to 10 carbon atoms, an arylene group of 6 to 10 carbon atoms or a heterocyclic group of 5 to 6 members with at least one atom selected from nitrogen, oxygen, and sulfur, and $M^2$ and $M^3$ are alkali metal ions.

9. The method of claim 8 wherein $Z^1$ is an arylene group, and $M^2$ and $M^3$ are sodium or potassium.

10. The method of claim 6 wherein the silver halide emulsion is greater than 90 mole % silver chloride.

11. The method of claim 6 wherein the sulfur donating compound is an aryldialkylamino disulfide, an acyl-methylmercapto azolium salt, a 1,2,3,4-thiatriazole, a theipin, a diamino disulfide or a thiosulfonate salt.

12. The method of claim 6 wherein the amount of sulfur donating compound added is from $10^{-3}$ to 1 g/mol Ag and the amount of the disulfinate compound added is from $10^{-2}$ to 10 g/mol Ag.

13. The method of claim 6 wherein the ratio of the disulfinate compound added to the sulfur donating compound added is greater than 1:1.

14. The method of claim 6 wherein the sulfur donating compound is an aryldialkylamino disulfide, an acyl-methylmercapto azolium salt, a 1,2,3,4-thiatriazole, a theipin, an aminodisulfide or a thiosulfonate salt;

$Z^1$ is an alkylene group of 1 to 20 carbon atoms, an arylene group of 6 to 20 carbon atoms or a heterocyclic group of 5 to 15 members with at least one atom selected from nitrogen, oxygen, sulfur, selenium and tellurium, and $M^2$ and $M^3$ are alkali metal or ammonium ions;

the amount of sulfur donating compound added is from $10^{-3}$ to 1 g/mol Ag; and the amount of disulfinate compound added is from $10^{-2}$ to 10 g/mol Ag.

15. The method of claim 14 wherein $Z^1$ is an alkylene group of 1 to 10 carbon atoms, an arylene group of 6 to 10 carbon atoms or a heterocyclic group of 5 to 6 members with at least one atom selected from nitrogen, oxygen, and sulfur, $M^2$ and $M^3$ are alkali metal ions; and wherein the ratio of the disulfinate compound added to the sulfur donating compound added is greater than 1:1.

* * * * *